US008685438B2

(12) United States Patent
Murray et al.

(10) Patent No.: US 8,685,438 B2
(45) Date of Patent: Apr. 1, 2014

(54) COMPOSITIONS, KITS, AND METHODS UTILIZING AN ADDED BORON SOURCE

(75) Inventors: Sean Michael Murray, Springboro, OH (US); Tracy Ann Murray, legal representative, Springboro, OH (US); Gregory Dean Sunvold, Lewisburg, OH (US); Elizabeth Anne Flickinger, Dayton, OH (US)

(73) Assignee: The Iams Company, Cincinnati, OH (US)

( * ) Notice: Subject to any disclaimer, the term of this patent is extended or adjusted under 35 U.S.C. 154(b) by 1519 days.

(21) Appl. No.: 11/074,100

(22) Filed: Mar. 7, 2005

(65) Prior Publication Data

US 2005/0208105 A1 Sep. 22, 2005

Related U.S. Application Data

(60) Provisional application No. 60/553,754, filed on Mar. 17, 2004.

(51) Int. Cl.
*A23K 1/17* (2006.01)
*A61K 31/69* (2006.01)

(52) U.S. Cl.
USPC ............................................ 424/442; 514/64

(58) Field of Classification Search
USPC ..................... 424/84, 442; 426/54; 514/64
See application file for complete search history.

(56) References Cited

U.S. PATENT DOCUMENTS

| 4,849,220 | A | | 7/1989 | Nielsen et al. | |
|---|---|---|---|---|---|
| 5,480,638 | A | * | 1/1996 | Erwin | 424/84 |
| 5,958,475 | A | | 9/1999 | Ju et al. | |
| 5,962,049 | A | * | 10/1999 | Miljkovic | 426/74 |
| 2002/0010156 | A1 | | 1/2002 | Kennedy et al. | |
| 2002/0182276 | A1 | * | 12/2002 | Wadsworth et al. | 424/765 |
| 2003/0138547 | A1 | * | 7/2003 | Bui et al. | 426/630 |
| 2005/0042338 | A1 | * | 2/2005 | Tucker et al. | 426/115 |

FOREIGN PATENT DOCUMENTS

| AU | 200014959 A1 | | 8/2000 |
|---|---|---|---|
| DE | 19836450 A1 | | 2/2000 |
| EP | 0 497 287 B1 | | 5/1992 |
| SU | 803-934 | | 2/1981 |
| WO | WO 83/01559 A1 | | 5/1983 |
| WO | WO 92/12714 A2 | | 8/1992 |
| WO | WO00/51443 | * | 9/2000 |
| WO | WO03/022295 A | | 3/2003 |

OTHER PUBLICATIONS

Stanley, Jr. et al., "Effects of Boron and Selenium on Mallard Reproduction and DucklingGrowth and Survival", *Environmental Toxicology and Chemistry*, vol. 15, No. 7, pp. 1124-1132, 1996.

Forrest H. Nielsen, "The Saga of Boron in Food: From a Banished Food Preservative to a Beneficial Nutrient for Humans", *Current Topics in Plant Biochemistry and Physiology*, vol. 10, pp. 274-286, 1991.

Meacham et al., "Effect of Boron Supplementation on Blood and Urinary Calcium, Magnesium, and Phosphorus, and Urinary Boron in Athletic and Sedentary Women", *Am. J. Clin. Nutr* 1995; 16:341-345.

Forrest H. Nielsen, "Boron—An Overlooked Element of Potential Nutritional Importance", *Nutrition Today*, Jan./Feb. 1988, pp. 4-7.

Forrest H. Nielsen, "Facts and Fallacies About Boron", *Nutrition Today*, May/June, pp. 6-12 1992.

Naghii et al., "The Effect of Boron Supplementation on Its Urinary Excretion and Selected Cardiovascular Risk Factors in Healthy Male Subjects", *Biological Trace Element Research*, vol. 56, pp. 273-286, 1997.

Curtiss D. Hunt, "The Biochemical Effects of Physiologic Amounts of Dietary Boron in Animal Nutrition Models", *Environmental Health Perspectives*, vol. 102, Supplement 7, pp. 35-43, Nov. 1994.

Dufour et al., "Experimental Exposure of Broiler Chickens to Boric Acid to Assess Clinical Signs and Lesions of Toxicosis", *Avian Diseases*, vol. 36, pp. 1007-1011, 1992.

Basoglu et al., "Short Communication: Effect of Borax on Seerum Lipid Profile in Dogs", *Online Journal of Veterinary Research*, vol. 4(6): 146-148, 2000.

Naghii et al., "The Effect of Boron Supplementation on the Distribution of Boron in Selected Tissues and on Testosterone Synthesis in Rats", *Journal Nutritional Biochemistry*, vol. 7, pp. 507-512, 1996.

Naghii et al., "The Effect of Boron on Plasma Testosterone and Plasma Lipids in Rats", *Nutrition Research*, vol. 17, No. 3, pp. 523-531, 1997.

Seaborn et al., "Boron and Silicon: Effects on Growth, Plasma Lipids, Urinary Cyclic Amp and Bone and Brain Mineral Composition of Male Rats", *Environmental Toxicology and Chemistry*, vol. 13, No. 6, pp. 941-947, 1994.

Elliot et al., "Metabolism and Nutrition: Studies to Determine Whether an Interaction Exists Among Boron, Calcium, and Cholecalciferol on the Skeletal Development of Broiler Chickens", *Poultry Science*, vol. 71, pp. 677-690, 1992.

Sheng et al., "Dietary Boron Supplementation Enhances the Effects of Estrogen on Bone Mineral Balance in Ovariectomized Rats", *Biological Trace Element Research*, vol. 81, pp. 29-45, 2001.

Vashishtha et al., "Effect of Supplemental Boron on Nutrient Utilization, Mineral Status and Blood Biochemical Constituents in Lamabs Fed High Fluorine Diet", *Fluoride*, vol. 30, No. 3, pp. 165-172, 1997. Research Report 165.

Wilson et al., "Long Term Effects of Boron on Layer Bone Strength and Production Parameters", *British Poultry Science*, vol. 39, pp. 11-15, 1998.

XP002334002 (JP 2002 238468 A) (abstract), Aug. 27, 2002, Unitika Ltd.

* cited by examiner

*Primary Examiner* — Aradhana Sasan
(74) *Attorney, Agent, or Firm* — Amy M. Foust

(57) ABSTRACT

Disclosed here are methods, compositions, and kits which are useful for weight management benefits in the mammal. Each of the methods, compositions, and kits utilize an added boron source.

6 Claims, No Drawings

COMPOSITIONS, KITS, AND METHODS UTILIZING AN ADDED BORON SOURCE

CROSS REFERENCE

This application claims the benefit of U.S. Provisional Application No. 60/553,754 filed on Mar. 17, 2004.

FIELD OF THE INVENTION

The present invention is directed to compositions, kits, and methods which are particularly useful for weight management in a mammal. The various embodiments of the invention utilize a boron source to achieve this purpose.

BACKGROUND OF THE INVENTION

The management of weight in mammals, particularly those mammalian populations which are advanced in age or those companion animals which have been spayed or neutered, is a complex problem which needs to be addressed for a variety of health concerns, including secondary health concerns such as onset of diabetes or conditions of the cardiovascular system. For example, even when food intake is controlled and well-balanced, susceptible populations will still tend to experience issues with weight gain and such other secondary health concerns.

A variety of treatments have been proposed in the art, with limited or unacceptable efficacy, often involving restriction of food intake or exercise regimens. In populations wherein such restriction or regimens is impractical, for example in companion animals, alternative solutions need to be developed. These solutions should be in the form of therapies which actively assist with the management of weight even in populations where these other treatments are impractical or ineffective.

Boron has been extensively studied in terms of its effect on joint and bone health. Many studies have been conducted which indicate that this essential nutrient may have beneficial effects, particularly in aging or other post-menopausal populations. Many studies which have investigated the effects of boron on bone health have reported effects on weight as a routine, incidental, measure of the study.

Many of these studies have reported weight gain in animals ingesting non-excessive or non-toxic levels of boron. See e.g., Wilson and Ruszler, "Long Term Effects of Boron on Layer Bone Strength and Production Parameters," *British Poultry Science*, Vol. 39, pp. 11-15 (1998); Vashishtha et al., "Effect of Supplemental Boron on Nutrient Utilization, Mineral Status and Blood Biochemical Constituents in Lambs Fed High Fluorine Diet," *Fluoride*, Vol. 30, No. 3, pp. 165-172 (1997); Naghii and Samman, "The Effect of Boron Supplementation on the Distribution of Boron in Selected Tissues and on Testosterone Synthesis in Rats," *Nutritional Biochemistry*, Vol. 7, pp. 507-512 (1996) (hereinafter referenced as "Naghii 1"); and Naghii and Samman, "The Effect of Boron on Plasma Testosterone and Plasma Lipids in Rats," *Nutrition Research*, Vol. 17, No. 3, pp. 523-531 (1997) (hereinafter referenced as "Naghii 2"). Other studies which have incidentally reported weight effects in studies having other primary objectives have reported no significant effects on weight gain with boron supplementation (e.g., an overall weight gain with or without boron supplementation). See e.g., Sheng et al., "Dietary Boron Supplementation Enhances the Effects of Estrogen on Bone Mineral Balance in Ovariectomized Rats," *Biological Trace Element Research*, Vol. 81, pp. 29-45 (2001); Elliot and Edwards, "Studies to Determine Whether an Interaction Exists Among Boron, Calcium, and Cholecalciferol on the Skeletal Development of Broiler Chickens," *Poultry Science*, Vol. 71, pp. 677-690 (1992); Naghii 1; and Naghii 2. Even further, other studies incidentally reporting weight effects but having other primary objectives (such as those studying boron toxicity) have reported weight loss with boron supplementation, but in instances where 'excessive' or 'toxic' doses of boron were utilized. See e.g., Seaborn and Nielsen, "Boron and Silicon: Effects on Growth, Plasma Lipids, Urinary Cyclic AMP and Bone and Brain Mineral Composition of Male Rats," *Environmental Toxicology and Chemistry*, Vol. 13, No. 6, pp. 941-947 (1994).

Quite unexpectedly, particularly in view of conflicting reports in the literature, the present inventors have discovered that supplementation of boron provides a significant weight management benefit in mammals. Particularly interesting is the discovered effect of boron on geriatric or neutered mammals, which are ordinarily susceptible to excessive weight gain. The invention resulting from this discovery is described herein.

SUMMARY OF THE INVENTION

The present invention is directed to compositions, methods, and kits useful for the management of weight in a mammal. In one embodiment herein, the invention is directed to pet food compositions comprising an added boron source (for example, daily ration or nutritionally balanced pet food compositions as well as supplements).

In other embodiments, the invention is directed to methods of providing a weight management benefit in a mammal comprising orally administering to the mammal a composition comprising an added boron source.

Even further embodiments are directed to kits comprising a pet food composition comprising an added boron source; and information that the pet food composition provides a weight management benefit. Other kits comprise a composition which comprises an added boron source; and information that the composition provides a benefit selected from the group consisting of neutered mammal benefits, geriatric mammal benefits, and combinations thereof.

These and other aspects of the invention are described herein.

DETAILED DESCRIPTION OF THE INVENTION

Various documents including, for example, publications and patents, are recited throughout this disclosure. All such documents are hereby incorporated by reference. The citation of any given document is not to be construed as an admission that it is prior art with respect to the present invention.

All percentages and ratios are calculated by weight unless otherwise indicated. All percentages and ratios are calculated based on the total composition unless otherwise indicated.

Referenced herein are trade names for components including various ingredients utilized in the present invention. The inventors herein do not intend to be limited by materials under a certain trade name. Equivalent materials (e.g., those obtained from a different source under a different name or reference number) to those referenced by trade name may be substituted and utilized in the descriptions herein.

In the description of the invention various embodiments or individual features are disclosed. As will be apparent to the ordinarily skilled practitioner, all combinations of such embodiments and features are possible and can result in preferred executions of the present invention.

The compositions herein may comprise, consist essentially of, or consist of any of the features or embodiments as described herein.

While various embodiments and individual features of the present invention have been illustrated and described, various other changes and modifications can be made without departing from the spirit and scope of the invention. As will also be apparent, all combinations of the embodiments and features taught in the foregoing disclosure are possible and can result in preferred executions of the invention.

As used herein, the term "added boron source" means a boron source which is present in the referenced pet food composition as an additive ingredient.

As used herein, the term "companion animal" means a domestic animal preferably including (for example) dogs, cats, horses, cows, pigs, rabbits, and the like. Domestic dogs and cats are particularly preferred.

As used herein, the term "geriatric mammals" or the like includes mammals which are considered middle-aged or older in accordance with standards commonly utilized in the art, with the following proviso: a geriatric dog is a dog at the age of about 5 or above; and a geriatric cat is a cat at the age of about 7 or above.

As used herein, the term "geriatric mammal benefit" or the like includes benefits which are of particular use or significance to geriatric mammals. For example, it may be particularly useful to convey information to the owner of a companion animal that a composition herein is beneficial for the geriatric companion animal such as a geriatric dog or cat. For example, it may be particularly useful to convey information to the owner of a companion animal that a composition herein is beneficial for the geriatric companion animal such as a geriatric dog or cat. For example, such benefits may include weight management benefits, particularly to geriatric companion animals.

As used herein, the term "neutered mammal" means a mammal, whether male or female, which has been castrated, spayed, ovariectomized, or otherwise fixed, not intact, or incapable of reproduction.

As also used herein, the term "neutered mammal benefit" or the like includes benefits which are of particular use or significance to neutered mammals (note that this term may be specific to a specific animal, for example, "neutered cat benefit" or "neutered dog benefit"). For example, it may be particularly useful to convey information to the owner of a companion animal that a composition herein is beneficial for the neutered companion animal such as a neutered dog or cat. For example, such benefits may include weight management benefits particularly to neutered companion animals.

As used herein, the term "pet food composition" means a composition that is intended for ingestion by a companion animal.

As used herein, the term "weight management benefit" or the like includes (but may not be limited to) those benefits selected from the group consisting of weight maintenance or control (including decreasing likelihood of gaining excessive weight, decreasing likelihood of accumulating excessive fat mass, decreasing food intake such as to decrease the likelihood of weight gain or adiposity gain), weight loss, and combinations thereof. In a particularly preferred embodiment, the term "weight management benefit" means weight maintenance or control. Weight management may be prophylactic, for example, in mammals susceptible to weight gain (e.g., geriatric or neutered mammals) or may be treatment, for example, in mammals in which weight gain should be actively reduced or controlled. For example, wherein weight maintenance or control is exhibited, a companion animal ingesting the referenced composition ad libitum over a one-month period of time experiences less weight gain relative to a similar companion animal ingesting a composition which is not described as part of this invention ad libitum over the same period of time.

Compositions of the Present Invention

The present invention utilizes an added boron source in all embodiments of this invention. Without intending to be limited by theory, the present inventors have discovered that inclusion of an added boron source in a composition utilized for oral administration to a mammal is useful for purposes of weight management. This unexpected finding is particularly useful for mammals in need of a weight management benefit, such as geriatric mammals or neutered mammals.

The present invention is particularly useful for the treatment or other use of companion animals, preferably dogs or cats (as used herein, dogs are domestic dogs and cats are domestic cats). As such, the present invention is particularly useful for geriatric dogs, geriatric cats, neutered dogs, or neutered cats. However, the invention is of course useful for the treatment of mammals, whether geriatric, neutered, or not, as has been described herein.

A variety of boron sources may be utilized herein, as will be well-understood by one of ordinary skill in the art. Non-limiting examples of boron sources suitable for use herein include boric acid, sodium borate (e.g., sodium borate decahydrate, BORAX®), boron citrate, boron glycinate, boron aspartate, boron-enriched yeast, and mixtures thereof. The most preferred boron sources for use herein are boric acid, boron citrate, and boron-enriched yeast.

In one embodiment herein, the added boron source is boron-enriched yeast. Any of a variety of yeast may be utilized, and will be well-known in the art, such as those of the *Saccharomyces* genera (including, for example, *Saccharomyces cerevisiae* (sometimes referred to as "Baker's yeast"), and *Candida utilis* (which may also be referred to as *Torulopsis utilis*). As well be well understood in the art, boron-enriched yeast enriched with boron, such as for example via cultivation in a fermentation medium enriched with boron prior to harvesting and drying. For example, such cultivation may be similar to processes utilized to prepare selenium-enriched yeast or chromium-enriched yeast, except that the growth medium contains boron. Inorganic sources of boron, such as for example boric acid, sodium borate (e.g., sodium borate decahydrate, BORAX®), boron citrate, boron glycinate, or boron aspartate may be used as the boron for this purpose.

For example, aerobic fermentation of *Saccharomyces cerevisiae* may be performed. The media may contain beet or cane molasses, added vitamins, nutritional salts, and/or other growth factors, as well as boron. Temperature is controlled, generally at temperatures from about 28° C. to about 30° C., and pH is also controlled. This may result in a cream yeast mixture that is pasteurized to kill the yeast, then separated from the fermentation media and dried to a powder. The fermentation process results in boron bound and/or unbound to the yeast; the yeast assimilates boron into its protein, cell membrane, and/or cell soluble components as it grows in the enriched media.

In certain embodiments, the compositions utilized herein may preferably comprise less than about 0.075% of the added boron source, by weight of the composition. In an even further embodiment, the compositions may preferably comprise from about 0.001% to about 0.075%, or from about 0.001% to about 0.06%, or from about 0.002% to about 0.03%, of the added boron source, all by weight of the composition.

In other embodiments, the compositions are pet food compositions comprising from about 0.001% to about 5%, or from about 0.001% to about 3%, or from about 0.01% to about 2% of the added boron source, all by weight of the composition. In yet other embodiments, such as wherein a boron-enriched yeast is utilized as the added boron source, the compositions are pet food compositions comprising from about 0.1% to about 12%, or from about 0.5% to about 10%, or from about 1% to about 7% of the added boron source, all by weight of the composition. The foregoing is distinguished from levels of elemental boron; in one embodiment, the compositions are pet food compositions comprising from about 0.001% to about 0.075%, or from about 0.001% to about 0.06%, or from about 0.002% to about 0.03% elemental boron, all by weight of the composition. The level of added boron source may be determined by one of ordinary skill in the art based on a variety of factors, for example, the form of the composition (e.g., whether a dry composition, semi-moist composition, wet composition, or supplement, or any other form or mixture thereof).

The compositions used herein are, in a preferred embodiment, pet food compositions. These will advantageously include foods intended to supply necessary dietary requirements, as well as treats (e.g., dog biscuits) or other food supplements. Optionally, the composition herein may be a pet food composition such as a dry composition (for example, kibble), semi-moist composition, wet composition, or any mixture thereof. Alternatively or additionally, the composition is a supplement, such as a gravy, drinking water, yogurt, powder, suspension, chew, treat (e.g., biscuits) or any other delivery form.

Moreover, in one embodiment the composition is nutritionally balanced. As used herein, the term "nutritionally balanced," with reference to the companion animal composition, means that the composition has known required nutrients to sustain life in proper amounts and proportion based on recommendations of recognized authorities in the field of companion animal nutrition.

The compositions used herein may optionally comprise one or more further components. Other components are beneficial for inclusion in the compositions used herein, but are optional for purposes of the invention. In one embodiment, the food compositions may comprise, on a dry matter basis, from about 20% to about 50% crude protein, alternatively from about 20% to about 40% crude protein, by weight of the food composition, or alternatively from about 20% to about 35% crude protein. The crude protein material may comprise vegetable proteins such as soybean, cottonseed, and peanut, or animal proteins such as casein, albumin, and meat protein. Non-limiting examples of meat protein useful herein include a protein source selected from the group consisting of beef, pork, lamb, poultry, fish, vegetable, and mixtures thereof.

Furthermore, the compositions may comprise, on a dry matter basis, from about 5% to about 40% fat, alternatively from about 10% to about 35% fat, by weight of the food composition.

The compositions of the present invention may further comprise a source of carbohydrate. Grains or cereals such as rice, corn, milo, sorghum, barley, wheat, and the like are illustrative sources.

The compositions may also contain other materials such as dried whey and other dairy by products.

Kits of the Present Invention

The present invention further relates to kits comprising a composition as described herein and certain information which is beneficially described to the user, or in the case on non-human animals, to the owner thereof. In one embodiment the present invention is directed to kits comprising:
(a) a pet food composition comprising an added boron source; and
(b) information that the pet food composition provides a weight management benefit.

In another embodiment herein, kits are provided which comprise:
(a) a composition which comprises an added boron source; and
(b) information that the composition provides a benefit selected from the group consisting of neutered mammal benefits, geriatric mammal benefits, and combinations thereof.

The kits of the present invention may comprise one or more of the referenced compositions together with information which informs a user of the kit, by words, pictures, and/or the like, that use of the kit will provide one or more benefits as described herein (for example, weight management or a neutered mammal benefit). Optionally, the kits may comprise further information including information regarding general health and/or general physiological benefits including, but not limited to, refreshment, satiety, or nutrition (including specific nutritional benefits), or information regarding the benefits of active ingredients other than boron sources. Such information need not utilize the actual words used herein, for example, "weight", "management", "control", "loss", "companion", or the like, but rather use of words, pictures, symbols, and the like conveying the same or similar meaning are contemplated within the scope of this invention.

In a particularly preferred embodiment, the information is printed on a container holding the composition, e.g., a bag, tin, can, bin, pouch, or like container. These preferred kits may be in the form of one container holding the composition, or may be obtained as a plurality of containers each holding the composition. For example, the kits may be obtained as one can, or cases of four, six, eight, twelve, or twenty-four cans co-packaged together.

Methods of the Present Invention

The methods of the present invention comprise orally administering (i.e., through ingestion) a composition of the present invention to a mammal, preferably a companion animal and most preferably a neutered companion animal, to provide one or more health benefits, weight management benefits, nutritive or organoleptic benefits, including neutered mammal benefits, geriatric mammal benefits, and combinations thereof. In particular, in one embodiment, the invention is directed to methods of providing a weight management benefit in a mammal comprising orally administering to the mammal a composition comprising an added boron source. In other embodiments, the invention is directed to methods of providing a weight management benefit in a mammal selected from the group consisting of neutered mammals, geriatric mammals, and combinations thereof comprising orally administering to the mammal a composition comprising an added boron source.

The compositions of the present invention are ingested by mammals, particularly companion animals and most particularly neutered companion animals, in need of (for example) weight management benefits, neutered mammal benefits, geriatric mammal benefits, a palatable food source, or means to satisfy hunger or nutritional needs. The compositions may also be ingested as a supplement to normal dietetic requirements.

As used herein, the term "orally administering" with respect to the mammal (preferably, the companion animal (preferably a dog or cat), and most preferably a neutered companion animal) means that the mammal ingests or a human is directed to feed, or does feed, the mammal one or more compositions herein. Preferably, the composition is a pet food composition. Wherein the human is directed to feed the composition, such direction may be that which instructs and/or informs the human that use of the composition may and/or will provide the referenced benefit, for example, a weight management benefit. For example, such direction may be oral direction (e.g., through oral instruction from, for example, a physician, veterinarian, or other health professional, or radio or television media (i.e., advertisement), or written direction (e.g., through written direction from, for example, a physician, veterinarian, or other health professional (e.g., scripts), sales professional or organization (e.g., through, for example, marketing brochures, pamphlets, or other instructive paraphernalia), written media (e.g., internet, electronic mail, or other computer-related media), and/or packaging associated with the composition (e.g., a label present on a container holding the composition). As used herein, "written" means through words, pictures, symbols, and/or other visible descriptors. Such information need not utilize the actual words used herein, for example, "weight", "management", "control", "loss", "companion", or the like, but rather use of words, pictures, symbols, and the like conveying the same or similar meaning are contemplated within the scope of this invention.

The compositions described herein may be used as a supplement to ordinary dietetic requirements or may serve as the primary food for the mammal (and, as such, the supplements or foods may be nutritionally balanced). Administration may be on as-needed or as-desired basis, for example, once-monthly, once-weekly, or daily (including multiple times daily). When utilized as a supplement to ordinary dietetic requirements, the composition may be administered directly to the mammal or otherwise contacted with or admixed with daily feed or food. When utilized as a daily feed or food, administration will be well-known to those of ordinary skill.

The amount of composition utilized may be dependent on a variety of factors, including the condition and/or age of the mammal, the quality of the pet food composition (where applicable), and size or breed of the mammal (where applicable). As guidance, a mammal may be administered daily at least about 0.001 mg/kg of the added boron source (wherein "mg/kg" indicates mg of added boron source per kilogram of mammal), or from about 0.001 mg/kg to about 20 mg/kg of the added boron source, or from about 0.01 mg/kg to about 15 mg/kg of the added boron source, or from about 0.1 mg/kg to about 12 mg/kg of the added boron source, or from about 1 mg/kg to about 10 mg/kg of the added boron source, or from about 1 mg/kg to about 5 mg/kg of the added boron source.

EXAMPLES

The following examples are provided to illustrate the invention and are not intended to limit the scope thereof in any manner.

Example 1

Two kibble compositions having the following components at the approximate indicated amounts are prepared using methods which are standard in the art and are fed to cats as a daily feed:

| Component | Example 1A (Component Amount indicated as Wt %) | Example 1B (Component Amount indicated as Wt %) |
| --- | --- | --- |
| Sodium Borate | 0.06 | 0.025 |
| Chicken, Chicken By-product Meal, and Fish Meal | 44 | 47 |
| Chicken Fat | 8 | 6 |
| Beet Pulp | 2 | 3 |
| Salts | 2.5 | 2 |
| Vitamins and Minerals* | 1 | 1 |
| Minors | 3.5 | 4 |
| Grains (corn, sorghum) | Remainder | Remainder |

*Vitamins and Minerals include: Vitamin E, beta-carotene and Vitamin A, Zinc Oxide, Ascorbic Acid, Manganese Sulfate, Copper Sulfate, Manganous Oxide, Calcium Pantothenate, Biotin, Vitamin $B_{12}$, Vitamin $B_1$, Niacin, Vitamin $B_2$, Vitamin $B_6$, Vitamin $D_3$, Folic Acid.

Example 2

A beef-flavor gravy composition is prepared by combining the following components in a conventional manner:

| Component | Wt % |
| --- | --- |
| Sodium Borate | 0.5 |
| Chicken Fat | 3.0 |
| Spray-Dried Beef Particles and Broth | 3.0 |
| Xanthan Gum | 0.5 |
| Flax Seed | 0.2 |
| Vegetables | 0.2 |
| Vitamins | 0.06 |
| Minerals | 0.04 |
| Phosphoric Acid | 0.95 |
| Beef Flavor | 0.1 |
| Water | Remainder |

*Vitamins and Minerals include: Vitamin E, beta-carotene and Vitamin A, Zinc Oxide, Ascorbic Acid, Manganese Sulfate, Copper Sulfate, Manganous Oxide, Calcium Pantothenate, Biotin, Vitamin $B_{12}$, Vitamin $B_1$, Niacin, Vitamin $B_2$, Vitamin $B_6$, Vitamin $D_3$, Folic Acid.

One fluid ounce of the gravy composition is admixed with one-half cup of standard dog kibble diet daily prior to feeding to a dog. Amounts of the gravy composition are determined as desired by the guardian of the dog.

Example 3

Weight management benefits and geriatric mammal benefits following administration of kibble compositions containing an added boron source are each studied in the cat. For the study, thirty gonadectomized cats within about 2% to about 3% of ideal body weight are used. Prior to gonadectomy, blood samples are taken to quantify levels of steroid hormone (estradiol, testosterone, progesterone). All cats are given a minimum of two weeks of recovery from gonadectomy prior to study initiation.

At initiation of the study period, cats are reassigned to one of three dietary treatment groups consisting of ten cats per group. Initial baseline measurements are taken on day zero and include recording of body weight, blood glucose and insulin levels, as well as blood collection for steroid hormones, initial CBC and blood chemistries.

Each treatment group is fed one of three test diets ad libitum that provide 0, 250, or 500 mg of added boron source/kg/day (wherein kg in this instance indicates kilogram diet). The feeding period is conducted for twelve weeks and allows for measurement of differences in weight gain, hormone levels (estradiol, testosterone, and progesterone) and glucose and insulin responses. During this time, weekly body weight measurements are taken to record weight status. Blood parameters are measured biweekly and DEXA scans are performed at the beginning and end of the trial on each cat. Results indicate that cats ingesting diets containing 500 mg added boron source/kg/day gain significantly less weight relative to the remaining cats; and further that cats ingesting diets containing 250 mg added boron source/kg/day gain significantly less weight relative to those cats ingesting diets containing 0 mg added boron source/kg/day.

What is claimed is:

1. A method of providing a weight management benefit in a neutered mammal, comprising orally administering to the mammal a food composition comprising at least about 250 mg per 1 kg of the composition an added boron source selected from the group consisting of boric acid, sodium borate, sodium borate decahydrate, boron citrate, boron glycinate, boron aspartate, boron-enriched yeast, and mixtures thereof.

2. The pet food composition according to claim 1 wherein the added boron source is boron-enriched yeast.

3. The pet food composition according to claim 1 comprising from about 0.5% to about 10% of the added boron source, by weight of the composition.

4. The pet food composition according to claim 3 comprising from about 1% to about 7% of the added boron source, by weight of the composition.

5. The method according to claim 1 wherein the mammal is a companion animal and the composition is a pet food composition.

6. The method according to claim 1 comprising administration of at least about 1 mg of added boron source per kg of the mammal.

* * * * *